United States Patent [19]
Naito et al.

[11] Patent Number: 4,927,964

[45] Date of Patent: May 22, 1990

[54] METHOD FOR PRODUCTION OF 2-OXYIMINO-3-OXOBUTYRIC ACIDS

[75] Inventors: Kenzo Naito, Kyoto; Yukio Ishibashi, Osaka; Haruo Shinbo, Hyogo, all of Japan

[73] Assignee: Takeda Chemical Industries, Ltd., Osaka, Japan

[21] Appl. No.: 295,510

[22] Filed: Jan. 11, 1989

[30] Foreign Application Priority Data

Jan. 18, 1988 [JP] Japan .................................. 63-9271

[51] Int. Cl.$^5$ .......................................... C07C 131/00
[52] U.S. Cl. ................................. 562/560; 548/342; 560/121; 560/123; 560/124; 560/125; 560/168; 562/503; 562/505; 562/506; 562/507

[58] Field of Search ............... 562/560, 503, 505, 506, 562/507; 560/121, 123, 124, 125, 168; 548/342

[56] References Cited

U.S. PATENT DOCUMENTS

4,107,380  8/1978  Wiesman ............................. 428/327
4,191,673  4/1980  Wiesman ............................. 524/524

*Primary Examiner*—Michael L. Shippen
*Attorney, Agent, or Firm*—Wegner & Bretschneider

[57] ABSTRACT

An advantageous method of producing in large amounts on a commercial scale 2-substituted oxyimino-3-oxobutyric acids, which are useful as intermediates in the synthesis of e.g. aminothiazole cephalosporins, is characterized by reacting a tert-butyl 2-substituted oxyimino-3-oxobutyrate with a hydrogen halide in an anhydrous organic solvent.

8 Claims, No Drawings

METHOD FOR PRODUCTION OF 2-OXYIMINO-3-OXOBUTYRIC ACIDS

This invention relates to an advantageous method of producing, in large amounts on a commercial scale, 2-substituted oxyimino-3-oxobutyric acids, which are useful as intermediates in the synthesis of cephalosporin compounds, among others.

2-Substituted oxyimino-3-oxobutyric acids are important intermediates in the synthesis of aminothiazole cephalosporins, typically cefmenoxime, for instance. Several aminothiazole cephalosporins are already on the market and in wide clinical use as antibiotics having a very broad antibacterial spectrum. Their structures, pharmacological activities and methods of production are described, for example, in Angewandte Chemie, International Edition in English, 24, 180–202 (1985) and Journal of Antibiotics, 38, 1738–1751 (1985). It is the 2-substituted oxyimino-3-oxobutyric acids that are used as intermediates in the synthesis of the aminothiazole moieties of the above-mentioned aminothiazole cephalosporins.

In the prior art, the 2-substituted oxyimino-3-oxobutyric acids are synthesized by hydrolyzing corresponding 2-substituted oxyimino-3-oxobutyric acid esters with an alkali such as sodium hydroxide [GB2012276] or hydrolyzing corresponding tert-butyl 2-substituted oxyimino-3-oxobutyrates with trifluoroacetic acid [U.S. Pat. No. 4107380, U.S. Pat. No. 4191673].

However, both the methods are not especially advantageous for large-quantity commercial production of 2-substituted oxyimino-3-oxobutyric acids. Thus, the method comprising hydrolyzing the starting 2-substituted oxyimino-3-oxobutyric acid esters with an alkali is disadvantageous in that it gives low yields, whereas the method which involves hydrolysis with trifluoroacetic acid is disadvantageous in that trifluoroacetic acid, which is an expensive reagent, must be used in excess.

As a result of their intensive investigations to elaborate a method of producing 2-substituted oxyimino-3-oxobutyric acids which is advantageous in large-quantity commercial production of the same, the present inventors found that the reaction of tert-butyl 2-substituted oxyimino-3-oxobutyrates with a hydrogen halide in an anhydrous organic solvent can give the desired 2-substituted oxyimino-3-oxybutyric acids in high purity and in high yield without using any expensive raw material and that, accordingly, the method involving said reaction is more advantageous as a method of producing 2-substituted oxyimino-3-oxobutyric acids at low costs than the known methods. Based on such findings, the present invention has now been completed.

The invention thus provides a method of producing 2-substituted oxyimino-3-oxobutyric acids which comprises reacting a tert-butyl 2-substituted oxyimino-3-oxobutyrate with a hydrogen halide in an anhydrous organic solvent.

Preferred examples of the tert-butyl 2-substituted oxyimino-3-oxobutyrate, which are the starting materials in carrying out the method according to the invention, are compounds of the formula

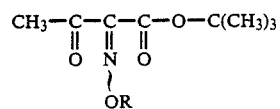

wherein R is a hydrogen atom or an alkyl group which may optionally be substituted. In compounds (I), the alkyl group represented by R is, for example, a straight or branched alkyl group having 1 to 4 carbon atoms, such as methyl, ethyl, propyl, isopropyl or butyl. The alkyl group represented by R may be substituted. Thus, said group may have one or two substituents each independently selected from the class consisting of a carboxyl group, $C_{1-4}$alkoxycarbonyl group (e.g. methoxycarbonyl, ethoxycarbonyl), cycloalkyl groups of 3 to 6 carbon atoms (e.g. cyclopropyl), heterocyclic groups (e.g. five-membered heterocyclic groups such as imidazol-5-yl) and the like. The "alkyl group which may optionally be substituted" as represented by R thus includes, among others, methyl, ethyl, cyclopropylmethyl, imidazol-5-ylmethyl, methoxycarbonylmethyl, ethoxycarbonylmethyl, 1-methoxycarbonyl-1-methylethyl and 1-ethoxycarbonyl-1-methylethyl. Typical examples of compounds (I) are tert-butyl 2-methoxyimino-3-oxobutyrate and the like.

Preferred examples of the desired product, namely 2-substituted oxyimino-3-oxobutyric acid, are compounds of the formula

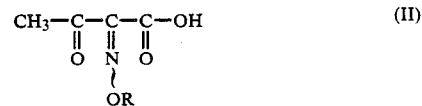

wherein R is as defined above. In formula (II), R represents a hydrogen atom or an alkyl group which may optionally be substituted, as mentioned above for formula (I). Typical examples of compounds (II) are 2-methoxyimino-3-oxobutyric acid and the like.

Usable as the hydrogen halide are hydrogen chloride, hydrogen bromide, and so on. Among them, hydrogen chloride is preferred, however.

The compounds (I) and (II) mentioned above each may be in the syn configuration

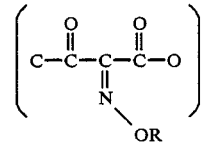

or in the anti configuration

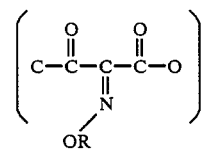

or in the form of a mixture of these. It is to be noted that any of the forms or configurations falls within the scope of the present invention.

The reaction is carried out in an anhydrous organic solvent. The organic solvent may be any one which will not adversely affect the reaction. Thus, usable as the organic solvent are, for example, nitriles such as acetonitrile, ethers such as tetrahydrofuran, 1,2-dimethoxyethane, dioxane and diethyl ether, halogenated hydrocarbons such as methylene chloride, chloroform, dichloroethane and carbon tetrachloride, esters such as ethyl acetate and butyl acetate, amides such as N,N-dimethylformamide and N,N-dimethylacetamide, hydrocarbons such as benzene, toluene, xylene, hexane and pentane, and mixtures of these. Among them, halogenated hydrocarbons (in particular, chlorinated hydrocarbons such as methylene chloride) are preferred in most cases. Such organic solvent is used generally in an amount of 0.1 to 10 liters, preferably 0.5 to 2 liters, per mole of tert-butyl 2-substituted oxyimino-3-oxobutyrate. Since the presence of water in the reaction mixture promotes byproduct formation, the quantity of water contained in the reaction mixture should advisably be as small as possible. For that reason, the organic solvent mentioned above should desirably be substantially anhydrous with the moisture content reduced as far as possible.

The reaction can be effected by bringing the tert-butyl 2-substituted oxyimino-3-oxobutyrate into contact with the hydrogen halide in the anhydrous organic solvent. Thus, the reaction is generally carried out by bringing the tert-butyl 2-substituted oxyimino-3-oxobutyrate into contact with the hydrogen halide, which is in the gaseous form, in the anhydrous organic solvent, for example by blowing the hydrogen halide gas into the mixture of the starting material and the solvent, if desired under pressure or with stirring. The reaction may also be effected by dissolving the hydrogen halide in advance in the anhydrous organic solvent employed, if desired under pressure or with stirring, and then adding the tert-butyl 2-substituted oxyimino-3-oxobutyrate to the thus-prepared solution. The hydrogen halide is used generally in an amount of 1 to 10 moles, preferably 1 to 6 moles, per mole of tert-butyl 2-substituted oxyimino-3-oxobutyrate, although said amount may vary depending on the organic solvent employed. When, in particular, an alkylene chloride, such as methylene chloride, which is preferred as the organic solvent, is used, the hydrogen halide is used generally in an amount of 1 to 3 moles, preferably 1.2 to 2 moles, per mole of tert-butyl 2-substituted oxyimino-3-oxobutyrate.

The reaction temperature is not critical. The only requirement is that the reaction can proceed at the temperature employed. Generally, however, the reaction is carried out at −50° C. to 80° C., preferably 0° C. to 30° C. The hydrogen halide is blown into the starting material-solvent mixture generally over a period of 0.5 to 20 hours, preferably 2 to 10 hours, although the period of hydrogen halide feeding should be varied depending on the reaction temperature, the solvent and the hydrogen halide quantity. Then, the reaction mixture is preferably stirred or allowed to stand generally for 1 to 24 hours, preferably 2 to 15 hours. In cases where the hydrogen halide is dissolved in advance in the solvent, for example by blowing into the solvent, the mixture obtained after addition of tert-butyl 2-substituted oxyimino-3-oxobutyrate should advantageously be stirred generally for 1 to 40 hours, preferably 2 to 20 hours.

The 2-substituted oxyimino-3-oxobutyric acid formed as a result of the reaction can be used as an intermediate for syntheses either in the form of the reaction mixture as it is or after isolation from the reaction mixture and purification by known means such as concentration, pH adjustment, solvent extraction, crystallization, recrystallization, chromatography, etc.

In an example of the use as intermediate for syntheses, the 2-substituted oxyimino-3-oxobutyric acid obtained by the method according to the invention is reacted, for example, with a halogenating agent in the presence of an anhydrous acid catalyst to give a 4-halo-2-substituted oxyimino-3-oxobutyric acid, which is useful as an intermediate for syntheses, preferably a compound of the formula

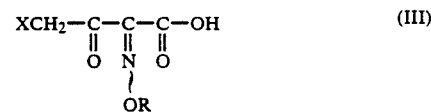

wherein X is a halogen atom, such as Cl, Br or I, and R is as defined above, the notation

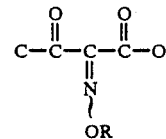

representing, as mentioned above, that compound (III) is in the syn or anti configuration or in the form of a mixture of the syn and anti forms.

Usable as the halogenating agent in the above reaction are, for example, halogens (chlorine, bromine, iodine), sulfuryl halides (sulfuryl chloride, etc.), N-halosuccinimides (N-bromosuccinimide, N-chlorosuccinimide, etc.) and 1,3-dibromo-5,5-dimethylhydantoin. Among them, bromine, sulfuryl chloride, N-bromosuccinimide and the like are preferred in most cases. Such halogenating agent is used generally in an amount of 0.5 to 1.5 moles per mole of 2-substituted oxyimino-3-oxobutyric acid. The halogenation reaction is generally carried out in a solvent. The solvent may be any one which will not adversely affect the reaction. Usable as the solvent are, for example, hydrocarbons, such as hexane, benzene, toluene and xylene, ethers, such as tetrahydrofuran, isopropyl ether, dioxane and diethyl ether, halogenated hydrocarbons, such as methylene chloride, chloroform and carbon tetrachloride, esters, such as ethyl acetate, ketones, such as acetone, amides, such as N,N-dimethylformamide and N,N-dimethylacetamide, and mixtures of these. Preferred as the solvent are halogenated hydrocarbons, such as methylene chloride, and ethers, such as tetrahydrofuran, among others. The reaction temperature is not critical. The only requirement is that the halogenation reaction can proceed at the temperature employed. Generally, a temperature of −50° C. to 80° C., preferably −20° C. to 30° C., is employed. The anhydrous acid catalyst is, for example, an inorganic acid, such as hydrogen chloride, hydrogen bromide, sulfuric acid, phosphoric acid or dichlorophosphoric acid, an organic acid, such as formic acid, acetic acid, p-toluenesulfonic acid, methanesulfonic acid or trifluoroacetic acid, or a Lewis acid, such as boron fluoride, aluminum chloride or titanium tetrachloride. That hydrogen bromide solution in acetic acid which is commercially available is a preferred example of the anhydrous acid catalyst. The 2-substituted oxyimino-3-oxobutyric acid formed by the method according to the invention can be subjected to said halogenation reaction in the form of the reaction mixture as it is and, in this case, the excess of the hydrogen halide used in carrying out the method according to the invention can serve as the anhydrous acid catalyst for the halogenation reaction. Therefore, when this halogenation reaction is conducted after carrying out the method according to the invention, 4-halo-2-substituted oxyimino-3-oxobutyric acids can be produced advantageously in large quantities on a commercial scale. The reaction time, which should be varied depending on the solvent used, the halogenating agent, the anhydrous acid catalyst, the reaction temperature and other factors, generally amounts to 0.5 to 20 hours, preferably 1 to 6 hours.

The thus-obtained 4-halo-2-substituted oxyimino-3-oxobutyric acid may be used as an intermediate for syntheses either in the form of the reaction mixture as obtained or after isolation and purification by known means, such as concentration, pH adjustment, solvent extraction, crystallization, recrystallization, chromatography, etc.

Typical examples of the 4-halo-2-substituted oxyimino-3-oxobutyric acid obtainable in the above manner are as follows:

(i) 4-Chloro-2-methoxyimino-3-oxobutyric acid,
(ii) 4-Bromo-2-methoxyimino-3-oxobutyric acid, and
(iii) 4-Iodo-2-methoxyimino-3-oxobutyric acid.

The method according to the invention is very useful as an industrial method of producing 2-substituted oxyimino-3-oxobutyric acids since it is superior to the prior art methods in the following respects, among others:

(1) That inexpensive starting materials can be used;
(2) That the desired products can be obtained in high purity and in high yield; and
(3) That the next step halogenation reaction can be performed advantageously.

As a result, the method according to the invention can serve as an advantageous method of producing synthetic intermediates for the commercial production of the desired end products in which the 2-substituted oxyimino-3-oxobutyric acids are used as intermediates. For instance, 7β-[2-(2-aminothiazol-4-yl)-(Z)-2-substituted oxyiminoacetamido]-3-unsubstituted or substituted-3-cephem-4-carboxylic acids or salts or esters thereof, which have excellent antimicrobial activity, can be derived from the 2-substituted oxyimino-3-oxobutyric acids obtained by the method according to the invention, for example, by halogenating the same in the above manner, reacting the thus-obtained 4-halo-2-substituted oxyimino-3-oxobutyric acids with thiourea, converting, if necessary, the resulting (Z)-2-substituted oxyimino-2-(aminothiazol-4-yl)acetic acids to reactive derivatives thereof having an activated carboxyl group and reacting such acids or reactive derivatives with a 7-amino-3-unsubstituted or substituted-3-cephem-4-carboxylic acid or a salt or ester thereof, or by converting, if necessary, the 4-halo-2-substituted oxyimino-3-oxobutyric acids to reactive derivatives thereof having an activated carboxyl group, reacting said acids or reactive derivatives with a 7-amino-3-unsubstituted or substituted-3-cephem-4-carboxylic acid or a salt or ester thereof and reacting the resulting reaction products with thiourea (U.S. Pat. No. 4098888, GB 1580621, U.S. Pat. No. 4166115, U.S. Pat. No. 4294960, U.S. Pat. No. 4278793, U.S. Pat. No. 4152433, GB 2012276, U.S. Pat. No. 4614819 and U.S. Pat. No. 4656287)

The following examples illustrate the invention in further detail but are by no means limitative of the scope of the invention.

The symbols used in the examples and reference example respectively have the following meanings:

s: singlet; CDCl$_3$: deuteriochloroform; %:% by weight; NMR (nuclear magnetic resonance) spectra were measured at 90 MHz with tetramethylsilane as an internal standard and the chemical shift values were given in terms of δ values (ppm).

EXAMPLE 1

Tertiary-butyl 2-methoxyimino-3-oxobutyrate (805 g) was dissolved in 2.8 liters of methylene chloride. Hydrogen chloride (210 g) was blown into the solution at 3° to 6° C. over 8 hours. Then, the resultant mixture was allowed to stand at 5° C. for 15 hours. The supernatant was concentrated to dryness to give 556 g of 2-methoxyimino-3-oxobutyric acid as a crystalline solid.

Yield 95.8%.

NMR (CDCl$_3$): δ 4.17 (3H, s), 2.44 (3H, s) ppm.

EXAMPLE 2

Hydrogen chloride was blown into 150 ml of 1,4-dioxane at 15° C. until a state of substantial saturation was attained. The hydrogen chloride solution thus obtained was diluted with 172 ml of 1,4-dioxane to give 363 ml of 4N hydrogen chloride solution in 1,4-dioxane.

A 200 ml portion of the above 4N hydrogen chloride solution in 1,4-dioxane was added to 35.0 g of tert-butyl 2-methoxyimino-3-oxobutyrate and the thus-obtained solution was stirred at 23° to 25° C. for 13 hours. The supernatant was concentrated, 200 ml of methylene chloride was added to the residue for dissolution of the latter, 30 ml of 20% aqueous sodium chloride was added to the thus-obtained supernatant, the mixture was shaken, and the organic layer was separated, dried over 12 g of anhydrous magnesium sulfate and concentrated to dryness under reduced pressure to give 21.8 g of 2-methoxyimino-3-oxobutyric acid.

Yield 86.4%.

The NMR spectrum of this product was in agreement with that obtained in Example 1.

REFERENCE EXAMPLE

In 3 liters of methylene chloride was dissolved 460 g of the 2-methoxyimino-3-oxobutyric acid obtained by the procedure of Example 1. To the solution was added 46 ml of a 25% hydrogen bromide solution in acetic acid. To the resultant solution was added dropwise over 2 hours at 7° to 15° C. a solution of 372 g of bromine in 372 ml of methylene chloride. Nitrogen was then blown into the mixture violently at 7° to 8° C. for 30 minutes so as to eliminate the byproduct hydrogen bromide. Silica gel (Kieselgel 60, 70 to 230 mesh, manufactured by Merck; 80 g) and activated carbon (Shirasagi of larger grain A grade, manufactured by Takeda Chemical Industries; 30 g) were added to the supernatant obtained. The mixture was stirred at 10° to 15° C. for 30 minutes and the insoluble matter was removed by filtration. The filtrate was concentrated under reduced pressure, the oily residue was dissolved in 685 ml of xylene, and the solution was allowed to stand at 5° C. for 15 hours. The resultant crystalline precipitate was collected by filtration, washed with 100 ml of a 1:1 (v/v) mixture of xylene and n-hexane and then with 200 ml of n-hexane, and dried under reduced pressure to give 434 g of 4-bromo-2-methoxyimino-3-oxobutyric acid. The filtrate (mother liquor) was concentrated under reduced pressure and the oily residue was crystallized by addition of 238 ml of a 100:15 (v/v) mixture of xylene and n-hexane to give 82.3 g of 4-bromo-2-methoxyimino-3-oxobutyric acid as a second crop.

Yield 72.7%.

NMR (CDCl$_3$): δ 4.36 (2H, s), 4.20 (3H, s) ppm.

What we claim is:

1. A method of producing a 2-substituted oxyimino-3-oxobutyric acid of the formula:

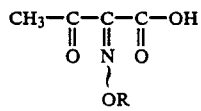

wherein R is a hydrogen atom or a straight or branched alkyl group having 1 to 4 carbon atoms which may be substituted with one or two members of the group selected from a carboxyl group, C$_{1-4}$ alkoxy-carbonyl group, a cycloalkyl group of 3 to 6 carbon atoms and a five-membered heterocyclic group, which comprises reacting a tert-butyl 2-substituted oxyimino-3-oxobutyrate of the formula:

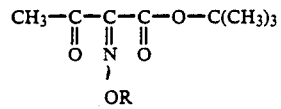

wherein R is as defined above, with a hydrogen halide in an anhydrous organic solvent.

2. A method according to claim 1, wherein the five-membered heterocyclic group is imidazol-5-yl.

3. A method according to claim 1, wherein the alkyl group which may optionally be substituted is methyl, ethyl, cyclopropylmethyl, imidazol-5-ylmethyl, methoxycarbonylmethyl, ethoxycarbonylmethyl, 1-methoxycarbonyl-1-methylethyl or 1-ethoxycarbonyl-1-methylethyl.

4. A method according to claim 1, wherein R is methyl.

5. A method according to claim 1, wherein the hydrogen halide is hydrogen chloride.

6. A method according to claim 1, wherein the anhydrous organic solvent in a nitrile, ether, halogenated hydrocarbon, ester, amide, hydrocarbon or a mixture thereof.

7. A method according to claim 1, wherein the anhydrous organic solvent is a halogenated hydrocarbon.

8. A method according to claim 7, wherein the halogenated hydrocarbon is methylene chloride.

* * * * *